United States Patent [19]
Chow

[11] Patent Number: 5,955,028
[45] Date of Patent: *Sep. 21, 1999

[54] ANALYTICAL SYSTEM AND METHOD

[75] Inventor: Calvin Y. H. Chow, Portola Valley, Calif.

[73] Assignee: Caliper Technologies Corp., Palo Alto, Calif.

[*] Notice: This patent is subject to a terminal disclaimer.

[21] Appl. No.: 08/911,310

[22] Filed: Aug. 14, 1997

Related U.S. Application Data

[63] Continuation-in-part of application No. 08/691,632, Aug. 2, 1996.

[51] Int. Cl.$^6$ .......................... G01N 21/00; G01N 21/25; G01N 21/62
[52] U.S. Cl. .......................... 422/63; 422/50; 422/82.09; 436/171; 204/600; 204/601
[58] Field of Search .................................. 422/63, 50, 52, 422/54, 55, 56, 67, 68.1, 82.05, 82.09, 88, 91; 436/165, 171, 101, 170; 204/600, 601, 450, 451

[56] References Cited

U.S. PATENT DOCUMENTS

| | | | |
|---|---|---|---|
| 4,726,929 | 2/1988 | Gropper et al. | 422/68 |
| 4,919,887 | 4/1990 | Wakatake | 422/67 |
| 5,030,418 | 7/1991 | Miyata | 422/63 |
| 5,049,359 | 9/1991 | Azuma et al. | 422/67 |
| 5,106,758 | 4/1992 | Adler et al. | 436/165 |
| 5,219,526 | 6/1993 | Long | 422/64 |
| 5,223,219 | 6/1993 | Subramanian et al. | 422/55 |
| 5,270,006 | 12/1993 | Uchigaki et al. | 422/63 |
| 5,304,487 | 4/1994 | Wilding et al. | 435/291 |
| 5,334,349 | 8/1994 | Kellen et al. | 422/63 |
| 5,344,326 | 9/1994 | Ferris | 434/336 |
| 5,443,790 | 8/1995 | Coeurveille et al. | 422/63 |
| 5,486,335 | 1/1996 | Wilding et al. | 422/55 |
| 5,489,414 | 2/1996 | Schreiber et al. | 422/64 |
| 5,498,392 | 3/1996 | Wilding et al. | 422/18.1 |
| 5,501,838 | 3/1996 | Ootani et al. | 422/65 |
| 5,510,082 | 4/1996 | Arai et al. | 422/64 |
| 5,519,635 | 5/1996 | Miyake et al. | 364/497 |
| 5,603,351 | 2/1997 | Cherukure et al. | 137/597 |
| 5,716,825 | 2/1998 | Hancock et al. | 435/286.5 |

FOREIGN PATENT DOCUMENTS

| | | |
|---|---|---|
| 0 006 031 | 12/1979 | European Pat. Off. . |
| 0 299 521 | 1/1989 | European Pat. Off. . |
| 0 616 218 | 9/1994 | European Pat. Off. . |
| WO 95/02189 | 1/1995 | European Pat. Off. . |
| 49-77693 | 7/1974 | Japan . |
| 3-094158 | 4/1991 | Japan . |
| 3-101752 | 4/1991 | WIPO . |
| WO 95/02189 | 1/1995 | WIPO . |
| WO 95/26796 | 10/1995 | WIPO . |
| 96/04547 | 2/1996 | WIPO . |
| WO 96/14934 | 5/1996 | WIPO . |

*Primary Examiner*—Lila Feisee
*Assistant Examiner*—Nirmal S. Basi
*Attorney, Agent, or Firm*—Matthew B. Murphy; James M. Heslin; Townsend and Townsend and Crew LLP

[57] ABSTRACT

An analytical or preparatory system comprised as a base unit, an adapter, and a substrate. The adapter is attached to an attachment region on the base unit, and the substrate is attached to an attachment region on the adapter. The adapter permits the base unit to be interfaced with a wide variety of different substrates to perform chemical and biological analytical analyses and preparatory procedures.

15 Claims, 4 Drawing Sheets

ANALYTICAL SYSTEM AND METHOD

This application is a continuation-in-part of application Ser. No. 08/691,632, filed on Aug. 2, 1996, the full disclosure of which is incorporated herein by reference.

BACKGROUND OF THE INVENTION

1. Field of the Invention

The present invention relates generally to systems and methods for performing chemical and biological analyses. More particularly, the present invention relates to the design and use of an analyzer system which employs analytical substrates evaluated in a base unit, where an adapter is used as an interface between the substrate and the base unit.

Numerous systems and instruments are available for performing chemical, clinical, and environmental analyses of chemical and biological specimens. Conventional systems may employ a variety of detection devices for monitoring a chemical or physical change which is related to the composition or other characteristic of the specimen being tested. Such instruments include spectrophotometers, fluorometers, light detectors, radioactive counters, magnetometers, galvanometers, reflectometers, ultrasonic detectors, temperature detectors, pressure detectors, mephlometers, electrophoretic detectors, PCR systems, LCR systems, and the like. Such instruments are often combined with electronic support systems, such as microprocessors, timers, video displays, LCD displays, input devices, output devices, and the like, in a stand-alone analyzer. Such analyzers may be adapted to receive a sample directly but will more usually be designed to receive a sample placed on a sample-receiving substrate, such as a dipstick, cuvette, analytical rotor or the like. Usually, the sample-receiving substrate will be made for a single use (i.e. will be disposable), and the analyzer will include the circuitry, optics, sample manipulation, and other structure necessary for performing the assay on the substrate. As a result, most analyzers are intended to work only with a single type of sample-receiving substrate and are not readily adaptable to be used with other substrates.

Recently, a new class sample-receiving substrate has been developed, referred to as "microfluidic" systems. Microfluidic substrates have networks of chambers connected by channels which have mesoscale dimensions, where at least one dimension is usually between 0.1 $\mu$m and 500 $\mu$m. Such microfluidic substrates may be fabricated using photolithographic techniques similar to those employed in the semiconductor industry, and the resulting devices can be used to perform a variety of sophisticated chemical and biological analytical techniques. Microfluidic analytical technology has a number of advantages, including the ability to employ very small sample sizes, typically on the order of nanoliters. The substrates may be produced at a relatively low cost, and can be formatted to perform numerous specific analytical operations, including mixing, dispensing, valving, reactions, and detections.

Because of the variety of analytical techniques and potentially complex sample flow patterns that may be incorporated into particular microfluidic test substrates, significant demands may be placed on the analytical units which support the test substrates. The analytical units not only have to manage the direction and timing of flow through the network of channels and reservoirs on the substrate, they may also have to provide one or more physical interactions with the samples at locations distributed around the substrate, including heating, cooling, exposure to light or other radiation, detection of light or other emissions, measuring electrical/electrochemical signals, pH, and the like. The flow control management may also comprise a variety of interactions, including the patterned application of voltage, current, or power to the substrate (for electrokinetic flow control), or the application pressure, acoustic energy or other mechanical interventions for otherwise inducing flow.

It can thus be seen that a virtually infinite number of specific test formats may be incorporated into microfluidic test substrates. Because of such variety and complexity, many if not most of the test substrates will require specifically configured analyzers in order to perform a particular test. Indeed, it is possible that particular test substrates employ more than one analyzer for performing different tests. The need to provide one dedicated analyzer for every substrate and test, however, will significantly reduce the flexibility and cost advantages of the microfluidic systems.

It would therefore be desirable to provide improved analytical systems and methods which overcome or substantially mitigate at least some of the problems set forth above. In particular, it would be desirable to provide analytical systems including base analytical units which can support a number of different microfluidic or other test substrates having substantially different flow patterns, chemistries, and other analytical characteristics. It would be particularly desirable to provide analytical systems where the cost of modifying a base analytical unit to perform different tests on different test substrates is significantly reduced.

2. Description of the Background Art

Microfluidic devices for analyzing samples are described in the following patents and published patent applications: U.S. Pat. Nos. 5,498,392; 5,486,335; and 5,304,487; and WO 96/04547. An analytical system having an analytical module which connects to an expansion receptacle of a general purpose computer is described in WO 95/02189. A sample typically present on an analytical rotor or other sample holder, may be placed in the receptacle and the computer used to control analysis of the sample in the module. Chemical analysis systems are described in U.S. Pat. Nos. 5,510,082; 5,501,838; 5,489,414; 5,443,790; 5,344,326; 5,344,349; 5,270,006; 5,219,526; 5,049,359; 5,030,418; and 4,919,887; European published applications EP 299 521 and EP 6 031; and Japanese published applications JP 3-101752; JP 3-094158; and JP 49-77693.

The disclosure of the present application is related to the following co-pending applications, the full disclosures of which are incorporated herein by reference, application Ser. Nos. 60/015498 (provisional), filed on Apr. 16, 1996; 08/671,987, filed on Jun. 28, 1996; 08/671,986, filed on Jun. 28, 1996; 08/678,436, filed on Jul. 3, 1996; and 08/683,080, filed Jul. 16, 1996.

SUMMARY OF THE INVENTION

The present invention overcomes at least some of the deficiencies described above by providing analytical and preparatory systems and methods which employ an adapter to interface between a sample substrate and an analytical base unit. The sample substrate is usually a microfluidic substrate but could be any other sample substrate capable of receiving test specimen(s) or starting material(s) for processing or providing a detectable signal, where the base unit manages sample flow, reagent flow, and other aspects of the analytical and/or preparatory technique(s) performed on the substrate. The adapter allows a single type of base unit, i.e. a base unit having a particular configuration, to interface with a large number of test and other substrates having quite different configurations and to manage numerous specific analytical and preparatory techniques on the substrates with little or no reconfiguration of the base unit itself.

The methods and apparatus will find use with both analytical and preparatory techniques. By "analytical," it is meant that the assay or process is intended primarily to detect and/or quantitate an analyte or analytes in a test specimen. By "preparatory," it is meant that the process is intended primarily to produce one or more products from one or more starting materials or reagents. The remaining description relates mainly to the analytical methods and devices, but for the most part, all technology described will be equally useful for preparing materials for other subsequent uses.

In a first aspect, the present invention provides an analytical system comprising a base unit having an attachment region with a base interface array including at least one interface component therein. An adapter that is configured to be removably attached to the attachment region of the base unit and has an adapter-base interface array which also includes an interface component. The adapter-base interface array mates with the base interface array when the adapter is attached to the base unit, and at least some of the interface components in each of the arrays will couple or mate with each other. The adapter further includes a sample substrate attachment region having an adapter-sample substrate interface array therein. The adapter-sample substrate interface array will usually also include at least one interface component (but in some cases could act primarily to position interface component(s) on the base units relative to interface component(s) on the sample substrate). A sample substrate is configured to be removably attached to the sample substrate attachment region of the adapter and itself includes a sample substrate interface array which usually includes at least one interface component. The interface component(s) in the sample substrate interface array will mate with corresponding interface component(s) in the adapter-sample substrate interface array and/or in the base interface array when the sample substrate is attached to the sample substrate attachment region.

By providing suitable interface components in each of the interface arrays, power and/or signal connections may be made between the base unit and the sample substrate in a virtually infinite number of patterns. In some cases, the base unit will provide only power and signal connections to the adapter, while the adapter will provide a relatively complex adapter-sample substrate interface array for managing flow, other operational parameters, and detection on the sample substrate. In other cases, however, the base interface array on the base unit may be more complex, including for example light sources, detectors, and/or high voltage power, and the adapter will be less sophisticated, often acting primarily to position the sample substrate relative to interface components on the base unit, channeling voltages, and allowing direct communication between the base unit and the sample substrate.

Exemplary interface components include electrical power sources, analog signal connectors, digital signal connectors, energy transmission sources, energy emission detectors, other detectors and sensors, and the like. Energy transmission sources may be light sources, acoustic energy sources, heat sources, cooling sources, pressure sources, and the like. Energy emission detectors include light detectors, fluorometers, UV detectors, radioactivity detectors, heat detectors (thermometers), flow detectors, and the like. Other detectors and sensors may be provided for measuring pH, electrical potential, current, and the like. It will be appreciated that the interface components will often be provided in pairs where a component in one array is coupled or linked to a corresponding component in the mating array in order to provide for the transfer of power, signal, or other information. The interface components, however, need not have such paired components, and often energy transmission sources or emission detectors will be provided without a corresponding interface component in the mating interface array.

The base unit, adapter and sample substrate will be configured so that they may be physically joined to each other to form the analytical system. For example, the attachment region in the base unit may be a cavity, well, slot, or other receptacle which receives the adapter, where the dimensions of the receptacle are selected to mate with the adapter. Similarly, the attachment region on the adapter may comprise a receptacle, well, slot, or other space intended to receive the sample substrate and position the substrate properly relative to the adapter and or base unit. The sample substrate will preferably employ mesoscale fluid channels and reservoirs, i.e. where the channels have at least one dimension in the range from 0.1 $\mu$m to 500 $\mu$m, usually from 1 $\mu$m to 100 $\mu$m. The present invention, however, is not limited to the particular manner in which the base unit, adapter, and substrate are attached and/or to the particular dimensions of the flow channels on one sample substrate.

Although described thus far as a three-tiered system, it should be understood that the additional components or "tiers" could be utilized. For example, additional carriers or adapters could be utilized for providing additional interface (s), such as a carrier for the sample substrate, where the carrier would be mounted within or attached to the adapter which is received on the base unit. Similarly, the attachment region in the base unit which receives the adapter may comprise a discrete component which is itself removably or permanently affixed to the base unit. Formation of the attachment region using a discrete component is advantageous since it facilitates standardization of the system. For example, the adapter-attachment region component could be manufactured separately, optionally at a single location, and/or otherwise prepared to strict specifications, both of which would help assure that the base units which incorporate such standardized attachment regions will be compatible with all corresponding adapters. The standardized adapter-attachment region could also be adapted to interconnect with other components of the base unit, such as heaters, cooling blocks, pin connections, and the like, thus facilitating interface with these elements. Thus, systems having four or more tiers fall within the scope of the present invention.

In a second aspect of the present invention, the analytical system comprises a base unit and a sample substrate, generally as described above. An adapter is configured to be removably attached to the attachment region of the base unit and includes an attachment region to removably receive the sample substrate. The adapter holds the sample substrate in a fixed position relative to the base unit and provides either (i) a connection path from an interface component in the base interface array to the substrate or (ii) a connection path from an interface component in the sample substrate array to the base unit. In this aspect of the present invention, the adapter can act primarily to position a sample substrate relative to the interface array in the base unit. For example, if the base unit interface array includes a light source and/or light detector, the adapter can properly position the sample substrate relative to the light source/detector in order to perform a desired measurement. The adapter could optionally but not necessarily provide further interface capabilities between the sample substrate and the base unit.

In yet another aspect of the present invention, adapters are provided for use in combination with base units and sample substrates, as described above. The adapter comprises an adapter body having an adapter-base interface array including at least one of power and signal connector(s) disposed to mate with corresponding connector(s) in the base interface array when the adapter is attached to the attachment region on the base unit. The adapter further includes a sample substrate attachment region having an adapter-sample substrate interface array including at least flow biasing connectors disposed to mate with corresponding regions in the sample substrate interface array when the sample substrate is attached to the attachment region of the adapter. The flow biasing connectors will commonly be electrodes for electrokinetic flow control in mesoscale and other microfluidic sample substrates, but could also be acoustic, pressure, or mechanical flow-producing components. The adapter-sample substrate interface array will frequently include interface components in addition to the flow biasing connectors, such as radiation emission and detection components positioned to interface with particular regions of the sample substrates.

The base unit may be self-contained, i.e. it may include all digital and/or analog circuitry as well as user input/output interfaces which are necessary for controlling an assay and producing assay results from the system. Often, however, it will be preferable to interface the base unit with a general purpose or conventional computer, where the computer can provide some or all of the control analysis, and/or reporting function(s) as well as some or all of the user interface. Usually, the computer will be a standard personal computer or workstation which operates on a standard operating system, such as DOS, Windows® 95, Windows® NT, UNIX, Macintosh, and the like. The computer will be able to provide a number of standard user input devices, such as a keyboard, hard disk, floppy disk, CD reader, as well as user outputs, such as screens, printers, floppy disks, writable CD output, and the like. Use of the computer is particularly advantageous since it can significantly reduce the cost of the base unit and allow significant upgrading of the computer component of the system while using the same base unit. Despite these advantages, in some instances it may be desirable to incorporate the interface and digital circuitry of a computer into the base unit of the present invention, allowing all of the capabilities of a conventional digital computer, but with perhaps less flexibility.

When the system of the present invention is controlled via digital circuitry, i.e. using a separate conventional computer interfaced with the base unit or using digital control circuitry incorporated within the base unit, it will usually be desirable to provide at least a portion of the operating instructions associated with any particular adapter and/or any particular sample substrate and assay format in a computer-readable form, i.e. on a conventional computer storage medium, such as a floppy disk, a compact disk (CD ROM), tape, flash memory, or the like. The medium will store computer readable code setting forth the desired instructions, where the instructions will enable the computer (which may be a separate or integral computer) to interface with the base unit and to control an assay performed by the base unit upon the sample present on a sample substrate held by an adapter received on the base unit. The present invention thus comprises the computer program itself in the form of a tangible medium, e.g. disk, CD, tape, memory, etc., which may be used in combination with the system of the present invention. The present invention further comprises systems which include an adapter as set forth above in combination with the tangible medium storing the computer instructions described above. The present invention still further comprises systems which are combinations of one or more sample substrates as generally set forth above, together with a tangible medium setting forth computer readable code comprising instructions as set forth above.

The computer program may be provided to the user pre-loaded onto the desired medium, usually a floppy disk or a CD ROM, or may alternatively be downloaded onto the medium by the user from a central location via a network, over phone lines, or via other available communication and transmission means. The program will then be incorporated onto the medium and be available for use in the systems and methods of the present invention.

In a still further aspect in the present invention, a method for configuring an analytical system comprises providing a base unit having an attachment region including at least one interface component therein. An adapter is removably attached to the attachment region of the base unit so that an interface component on the adapter mates with a corresponding interface component on the base unit. The adapter includes a sample substrate attachment region having at least one interface component therein, and a sample substrate is removably attached to the sample substrate attachment region on the adapter so that an interface component on the sample substrate mates with a corresponding interface component on the adapter. Usually, but not necessarily, the adapter is removably attached to the base unit by placing the adapter within a receptacle on the base unit, and the sample substrate is removably attached to the adapter by placing the sample substrate within a receptacle on the adapter. The sample substrate will preferably be a microfluidic device having a plurality of channels connecting a plurality of reservoirs and including flow biasing regions positioned at one of the reservoirs and/or channels. The base unit may then direct or manage flow in the substrate by providing flow control signals to the adapter. The flow control signals energize flow biasing regions on the adapter whereby corresponding flow biasing regions on the substrate are energized to control flow through the channels and among the reservoirs. For example, the flow control may be effected by electrically biasing electrodes on the sample substrate to cause electrokinetic flow control. Alternatively, the energizing step may comprise acoustically driving the flow biasing regions on the sample substrate. Usually, the adapter will include electromagnetic radiation sources and detectors for signal generation and detection in a variety of analytical techniques. Any of the above control steps may be implemented by providing computer readable code to an integral or separate computer which controls the analytical system.

DESCRIPTION OF THE SPECIFIC EMBODIMENTS

Figure 1:
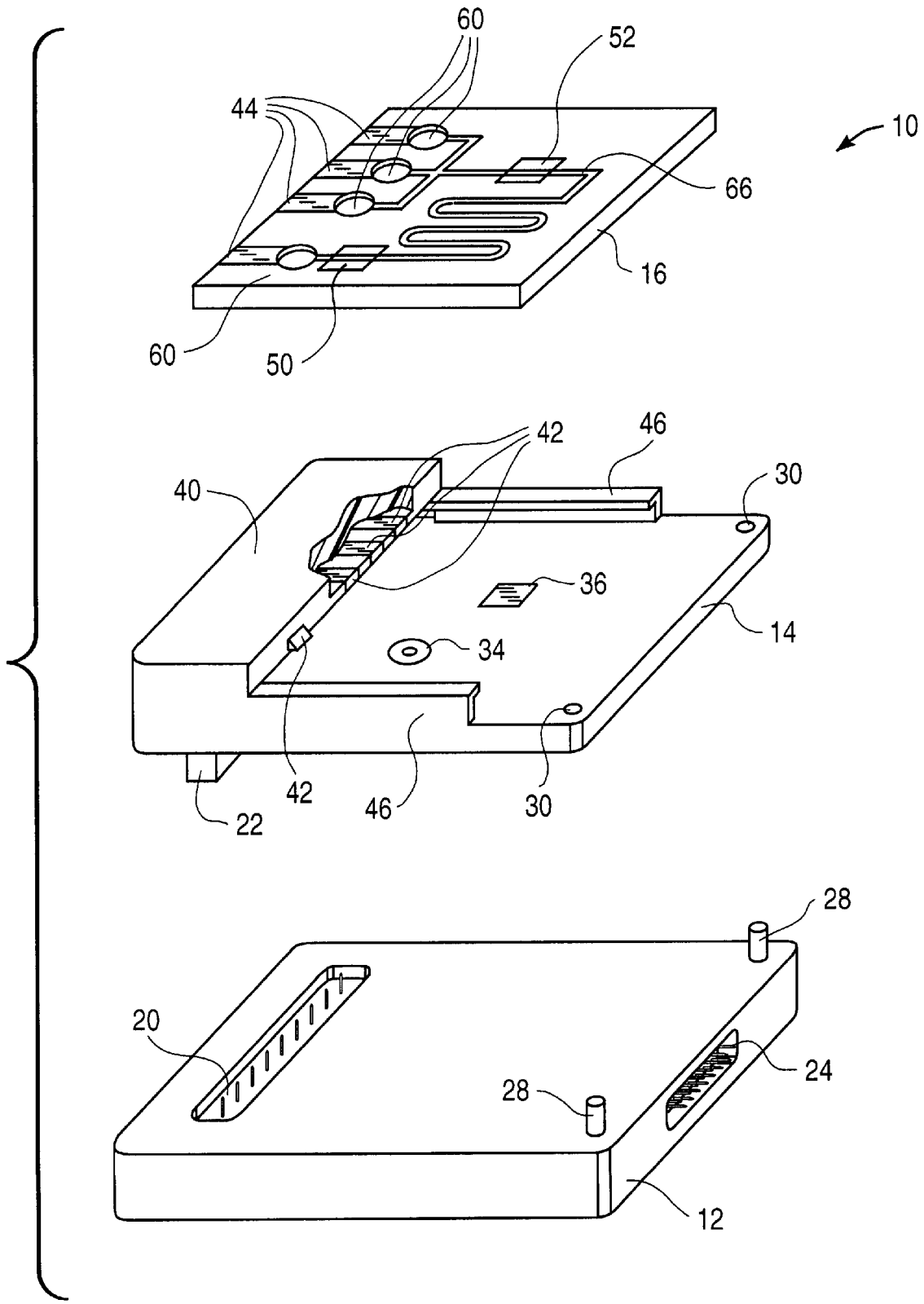
FIG. 1 illustrates a first embodiment of an analytical system incorporating the features of the present invention.

Analytical systems according to the present invention comprise a base unit, an adapter, and a sample substrate.

Each of these parts of the system will be described in detail below. In general, the analytical systems will be configured to receive and analyze a wide variety of samples and specimens. For example, samples may be biological specimens from a patient, but they may also be a wide variety of other biological, chemical, environmental, and other specimens having a component to be characterized or analyte to be detected. The analytical systems may be used to implement numerous specific analytical and/or preparative techniques, such as chromatography, PCR, LCR, enzymatic reactions, immunologic reactions, and the like. Samples will usually be liquid or be liquified prior to testing, and will frequently undergo a chemical or biochemical reaction prior to analysis. The analytical systems may provide for a variety of manipulations of the sample in addition to chemical and biological reactions, such as mixing, dispensing, valving, separation, heating, cooling, detection, and the like. The analytical systems may rely on numerous known detection techniques such as spectrophotometry, fluorometry, radiometry, magnatometry, galvanometry, reflectrometry, ultrasonic detection, mephlometry, electrophoretic measurement, temperature measurement, pressure measurement, potentiometric measurement, amperometric measurement, and the like. In the exemplary and preferred embodiments below, sample manipulation and detection are performed in microfluidic substrates where the sample is manipulated between and among very small volume reservoirs and flow channels formed in the substrate. Usually, all flow and test conditions on the substrate will be controlled through the base unit and the adapter, as described in more detail below.

The base unit of the present invention will typically comprise an enclosure or frame which may be intended for mounting, e.g. on the floor, on a counter, in a rack, or in any other conventional manner, or which may be portable or hand-held. The base unit will usually include at least power and/or signal transmission circuits, and will usually include signal processing capability for helping to analyze and/or store data received from the adapter as described in more detail below. The base unit will usually further include a microprocessor for helping manage both its substrate management and data collection duties. Optionally, information displays in the form of video monitors, alphanumeric displays, printers, LED displays, and the like, may be provided on or in the frame, often together with data entry devices, such as keyboards, touch screens, and the like. In the exemplary embodiments, however, the base unit includes only a plug connector for interfacing with an external computer, where the computer provides the necessary input and output devices. In such cases, the base unit will often, but not necessarily, include an internal microprocessor for controlling or helping to control the internal operations of the base unit and adapter. Alternatively, a microprocessor could be provided in the adapter, with the base unit providing only interface functions between the adapter and the computer. In other cases, all control functions will be managed through the separate computer with the base unit and adapter providing only distribution and interface functions. Again, it should be appreciated that availability of both the base unit and the adapter provides for a very wide range of specific designs with different functions being selectively distributed between the adapter and the base unit for particular assays and sample substrate designs.

The base unit will include an attachment region for removably securing the adapter. The attachment region on the base unit has a base interface array including at least one, and usually multiple, interface component(s) intended to provide power and/or information communication with the adapter. The interface component(s) comprise a wide variety of devices as described in more detail below. The attachment region may be any feature or structure on the enclosure or frame of the base unit which can removably attach the adapter. The attachment region will usually be constructed so that the adapter can be connected in a unique configuration only so that the base interface array will be uniquely configured relative to the adapter. The attachment region may have a wide variety of forms, such as receptacles, wells, slots, trays (similar to a CD tray), or the like. Often, the attachment region will define a receptacle having dimensions which correspond to the outer peripheral dimensions of the adapter so that the adapter may be held in a desired orientation relative to the base unit. Alternatively, or in addition, pegs, pins, latches, or other attachment elements may be provided to hold the adapter on the base unit in a desired orientation.

The adapter will also comprise an enclosure or frame, although the enclosure or frame will usually be significantly smaller than that of the base unit. The enclosure or frame will be adapted to be received on or in the attachment region of the base unit, as generally discussed above, and will itself include an attachment region for removably securing the sample substrate. The attachment region on the adapter may take any of the forms discussed above for the attachment region on the base unit, and it will usually be necessary for the attachment region to immobilize the sample substrate in a particular orientation relative to the adapter.

The adapter will include an adapter-base interface array which meets with or couples to the base interface array when the adapter is mounted in the attachment region on the base unit. The adapter-base interface array will include at least one interface component which mates with a corresponding interface component within the base interface array, usually to provide for power and/or signal connection between the base unit and the adapter. The interface component(s) may provide for a wide variety of additional interconnections, and will be described in greater detail below.

The sample substrate attachment region will include an adapter-sample substrate interface array intended to mate with or couple to a sample substrate interface array on the sample substrate when the sample substrate is attached to the attachment region. The adapter-sample substrate interface array will itself include at least one interface component which may be any of the components described in more detail below. Usually, the adapter-sample substrate interface array will include multiple interface components which are disposed or distributed in a pattern selected to mate with at least some corresponding interface component in the sample substrate array on the sample substrate.

The sample substrate may comprise any one of a variety of known analytical devices or articles intended for receiving a sample and processing the sample in some manner to provide a detectable output which can be related to a sample characteristic, e.g. the presence of an analyte, the composition or nature of a molecule present in the sample (e.g. protein or nucleic acid sequence), or the like. The present invention is particularly intended for use with microfluidic sample substrate of the type described in U.S. Pat. Nos. 5,498,392; 5,486,355; 5,304,487; and published PCT application WO 96/04547, the full disclosures of which are incorporated herein by reference. Suitable microfluidic substrates are also described in commonly assigned co-pending pending application Ser. Nos. 08/761,987, filed Jun. 28, 1996, and 08/845,759, filed Apr. 25, 1997, the full disclosures of which are incorporated herein by reference.

A particular advantage of the present invention is that the adapter can be configured to receive any one of a variety of specific sample substrate configurations. In that way, the designer of the sample substrate is free to optimize the size, design, flow paths, and other features of the sample substrate without undue regard to the nature of the base unit. Within a wide latitude, most specific design features of a sample substrate may be accommodated by appropriately designing an adapter. While this advantage is available, it is also possible that the design of the sample substrate take into account specific characteristics and design features of either or both of the base unit and adapter. It will be appreciated that the system architecture employing the adapter as an interface between the sample substrate and the base unit provides for significant design flexibility.

The sample substrate will have dimensions and other characteristics selected to permit removable attachment to the attachment region, as generally discussed above. Sample substrate will further include the substrate interface array which includes at least one interface component disposed to mate with a corresponding interface component on the adapter-sample substrate interface array on the adapter. Again, the interface components may comprise any of a wide variety of particular devices and elements, as discussed in more detail. The interface components on the adapter and sample substrate will generally be able to provide for both flow control management of the sample and other liquid reagents present in and applied to the sample substrate and will further provide for interconnection of power and signals between the adapter and sample substrate.

As used herein and in the claims, the phrase "interface component" refers to any one of a wide variety of discrete components or regions present in the interface arrays on the base unit, adapter, or sample substrate. Interface components will generally provide for electrical or other energy transfer, analog or digital signal transfer, energy transmission, energy emission detection, and the like.

Figure 2:
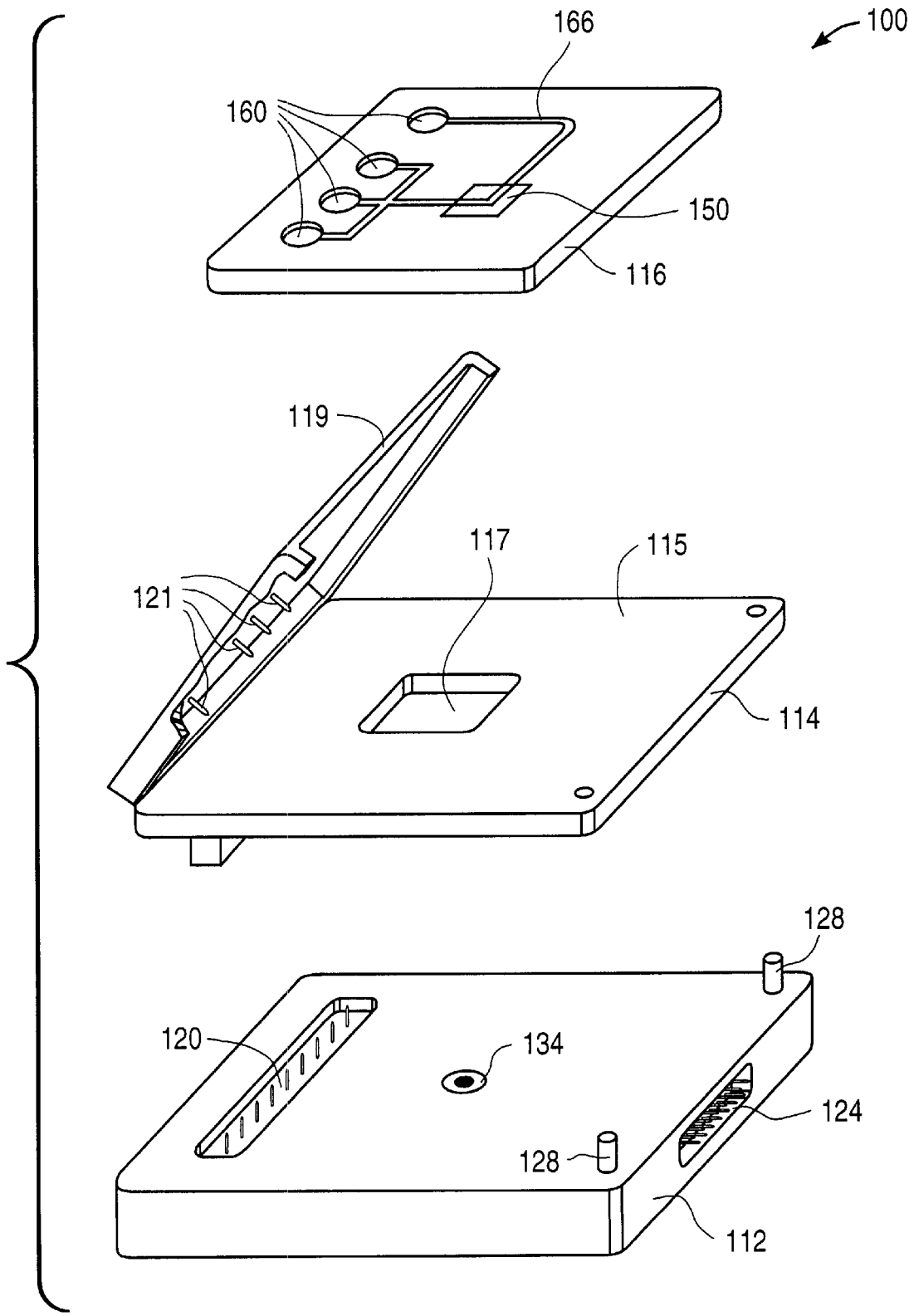
FIG. 2 illustrates a second embodiment of an analytical system incorporating the features of the present invention.

Electrical connections, both for power and signal transfer, will generally comprise conventional connectors in the form of electrodes, pins, plugs, zero insertion force (ZIF) connectors, and the like. Such electrical connections will usually require mating connectors in two of the interface arrays which are brought together when the system is put together. The electrical connectors will often be present on a surface or edge of the interface array so that corresponding components will be engaged against each other when the adapter is mounted in the base unit or the substrate is mounted on the adapter. Similarly, surface or edge electrodes in the adapter-sample substrate interface array may be provided to mate with corresponding surface or edge electrodes on the sample substrate. The electrodes on the sample substrate may then be connected internally in the substrate to the desired reservoirs or fluid flow channels in order to effect electrokinetic flow control, as described in the previously incorporated patents and patent applications. In other cases, however, it will be desirable to provide interface components in the adapter-sample substrate interface array which directly contact the fluid to be electrokinetically controlled. For example, probes or pins may be provided on the adapter which will penetrate into open wells or through septums on the sample substrate in order to permit direct contact and application of electrical potential. A specific example of such connectors are shown in FIG. 2 below.

The energy transmission sources will generally be intended to either energetically excite a region on the test substrate or provide energy to initiate fluid flow on the sample substrate. The energy may take a wide variety of forms, including light, such as visible light and UV light, acoustic energy, heat, cooling, pressure, mechanical energy, electrical energy, and the like. In the case of sample detection, the energy transmission source may be light or other radiation intended to excite a species or label to be detected. Heating/cooling may be provided to help effect or condition a particular chemical reaction. Acoustic, pressure, and mechanical energy may be provided to directly effect fluid flow in channels of microfluidic sample substrates. It will be appreciated that such energy transmission sources do not necessarily have corresponding interface components in an adjacent interface array. Instead, energy transmission will often be directed generally at regions on the sample substrate where energy is to be received.

Energy emission detectors may be provided, usually on the adapter and/or the base unit, to detect energy emitted from the sample substrate. For example, detection reactions may result in the emission of light via fluorescence, luminescence, radiation, or other energy emissions which need to be detected and/or quantified in order to perform particular analysis. The appropriate detection components may be provided in the adapter and/or base unit, and the adapter relied on to appropriately align the substrate the detectors.

A particular class of interface components employed by the analytical system of the present invention are referred to as "flow biasing connectors." Flow biasing connectors are intended to identify those interface components which can effect fluid flow on sample substrates, particularly on microfluidic substrates having a network of flow channels and reservoirs. For microfluidic substrates employing electrokinetic flow management, the flow biasing connectors on the adapter will usually be electrodes, probes, pins, or the like distributed within or on the adapter sample substrate interface array to mate with the network of flow channels and reservoirs in the sample substrate as generally described above and in the previously incorporated references. The electrodes will usually have corresponding electrode terminals present within the interface array on the sample substrate so that the electrode terminals may be interconnected to corresponding electrical connectors on the adapter-sample substrate interface array on the adapter (or in rare cases on the base interface array on the base unit). In other cases, as described above, the flow biasing connectors may be probes or pins on the adapter which are positioned to directly engage fluids present on or in the sample substrate. For example, an array of pins may be provided on a hinged lid or cover on the adapter plate so that the sample substrate may be positioned on the adapter and the lid cover thereafter closed in order to penetrate the pins into open sample wells on the substrate. The sample wells, of course, need not be open and could be covered with any penetratable membrane or septum which is pierced by the pins when the cover is closed. Other flow biasing connectors include acoustic energy sources (piezoelectric transducers) positioned within the adapter-sample substrate interface array so that they engage the sample substrate at positions intended to induce fluid flow through the flow channels. Other flow biasing connectors include pressure sources which can initiate flow by pressurization, mechanical energy sources, which can effect mechanical pumping of liquids through the flow channels, and the like.

Referring now to FIG. 1, a first exemplary analytical system 10 constructed in accordance with the principles of the present invention comprises a base unit 12, an adapter 14, and a sample substrate 16. The base unit 12 includes a pin socket 20 for mating with a plug 22 on a bottom surface of the adapter 14. A computer port 24 is provided for mating with conventional serial or parallel inputs on general purpose computers, such as personal computers, work stations, and the like. Usually, the base 12 will include at least signal processing and conditioning components, such as analog-to-digital converters for receiving analog data from the adapter 14 and converting that data to digital form for transmission to the computer. In other cases, however, the computer may be adapted to directly convert analog signals to digital data. The base unit 12 and/or adapter 14 could also be provided with digital-to-analog converters for controlling power, flow, or any other parameter directly from digital signals from the computer. The adapter 14 may also include internal microprocessor(s) for further data manipulation. The adapter 14 may also include a power input, for either line AC current and/or low voltage DC current (which may be provided by a power supply in the base unit 12). The pin socket 20 will usually provide for interface for both power and signal exchange between the base unit 12 and the adapter 14. Locating pins 28 are provided on an upper surface of the base 12 to engage locating holes 30 on the adapter 14. Thus, the entire upper surface of the base unit 12 will provide the attachment region for the adapter 14 while the pin socket 20 will generally provide the adapter-base interface array with the individual pins providing the interface components.

A plug 22 comprises the adapter-base interface array on the adapter 14. The plug 22 provides for both power and signal connections to the base unit 12 and the adapter further provides an optical source and detector 34 and a heating/cooling element 36, both of which mate to particular regions on the sample substrate 16, as described further below. The adapter 14 further includes an edge connector 40 which includes a number of electrodes 42 which mate with corresponding electrodes 44 on an edge of the sample substrate 16. The sample substrate 16 is removably attached to the adapter 14 by sliding the substrate between a pair of guides 46 which are formed by parallel L-shaped channels on the upper surface of the adapter 14. When the sample substrate 16 is fully inserted between the guides 46 with the electrodes 44 received in the edge connector 40, a reaction site 50 on the sample substrate 16 is aligned with the optical source of detector 34 on the adapter 14 and a thermal treatment region 52 is aligned with the heater/cooler 36 on the adapter. Thus, the optical source detector 34, heater/cooler 36, and edge connector 40 comprise interface components in the attachment region of the adapter 14.

The sample substrate 16 comprises a plurality of sample and reagent wells 60, each of which is coupled to an electrode 44 in the interface array. In this way, sample flow on the sample substrate can be controlled through the base unit 12 and the adapter 14 to control power through the electrodes 42. It will be appreciated that the power may be provided directly by the base unit 12, in which case the adapter 14 acts merely to distribute the power. Alternatively, the base unit 12 may provide information to the adapter, and the adapter 14 generate the power internally which is distributed through the electrodes 42. In either case, sample flow among the reservoirs and a flow channel network 66 is controlled in a desired manner. A portion of the sample and mixed reagents will flow through the heating/cooling region 52, where it will be appropriately treated. Again, the amount of heat or cooling supplied by region 36 is provided and controlled by a combination of the base unit 12 and adapter 14, where specific functions may be provided by either of those two components. An output signal resulting from one or more reactions is eventually read at the reaction region 50 by the optical source/detector 34. Output of the optical detector 34 will be passed back to the base unit 12 through the pin socket 20 and male plug 22. The optical detector will usually produce an analog signal, and such analog signal may be converted to digital in any of the adapter 14, base unit 12, or external computer (not shown).

A second exemplary embodiment 100 of the analytical system of the present invention is illustrated in FIG. 2. The analytical system 100 includes a base unit 112, an adapter 114, and a sample substrate 116. The base unit 112, is similar in many respects to base unit 12 in FIG. 1, and includes locating pins 128, a pin socket 120, and a computer port 124. Base unit 112, however, further comprises an optical source/detector 134. This is different than the analytical system 10, where the optical source/detector 34 was provided as part of the adapter 14.

The adapter 114 comprises a plate 115 having an aperture 117 in its center. When the adapter 114 is mounted on the base unit 112, the aperture 117 will lie generally over the optical source/detector 134. Adapter 114 further includes a hinged cover 119 which is used to cover and position the sample substrate 116 on top of the plate 115. When the sample substrate 116 is positioned, and the hinge cover 119 closed, a plurality of probes 121 on a lower surface of the cover will penetrate into sample and reagent wells 160 on the sample substrate 116. The wells 160 may be completely open or may be covered by a penetratable membrane or septum. The probes 121 will thus be immersed and in direct contact with the liquids present in the wells 160. In that way, electrical biasing can be provided in order to effect electrokinetic flow management through the channel network 166 on the sample substrate 116.

The sample substrate 116 includes a reaction zone 150 which will usually be at least partly transparent or translucent to permit light from the optical source detector 134 to reach the fluid in the region and to permit emitted or detected light to leave the region. Such incident and emitted light from region 150 will pass through the aperture 117 in the adapter 114 so that it may be directly coupled to the optical source/detector 134. Again, this is a difference with the analytical system 10 of FIG. 1 where detection was performed directly between the adapter 14 and the sample substrate 16.

It should be appreciated that the exemplary analytical systems 10 and 100 are intended to be representative of a virtually infinite number of possible system configurations. Use of an adapter 14 or 114 permits the various power, signal, and other functions of the analytical system to be included in any one of the adapter, base unit, substrate, or external computer in virtually any manner so that any particular analytical technique can be optimally supported by the system.

Figure 3:
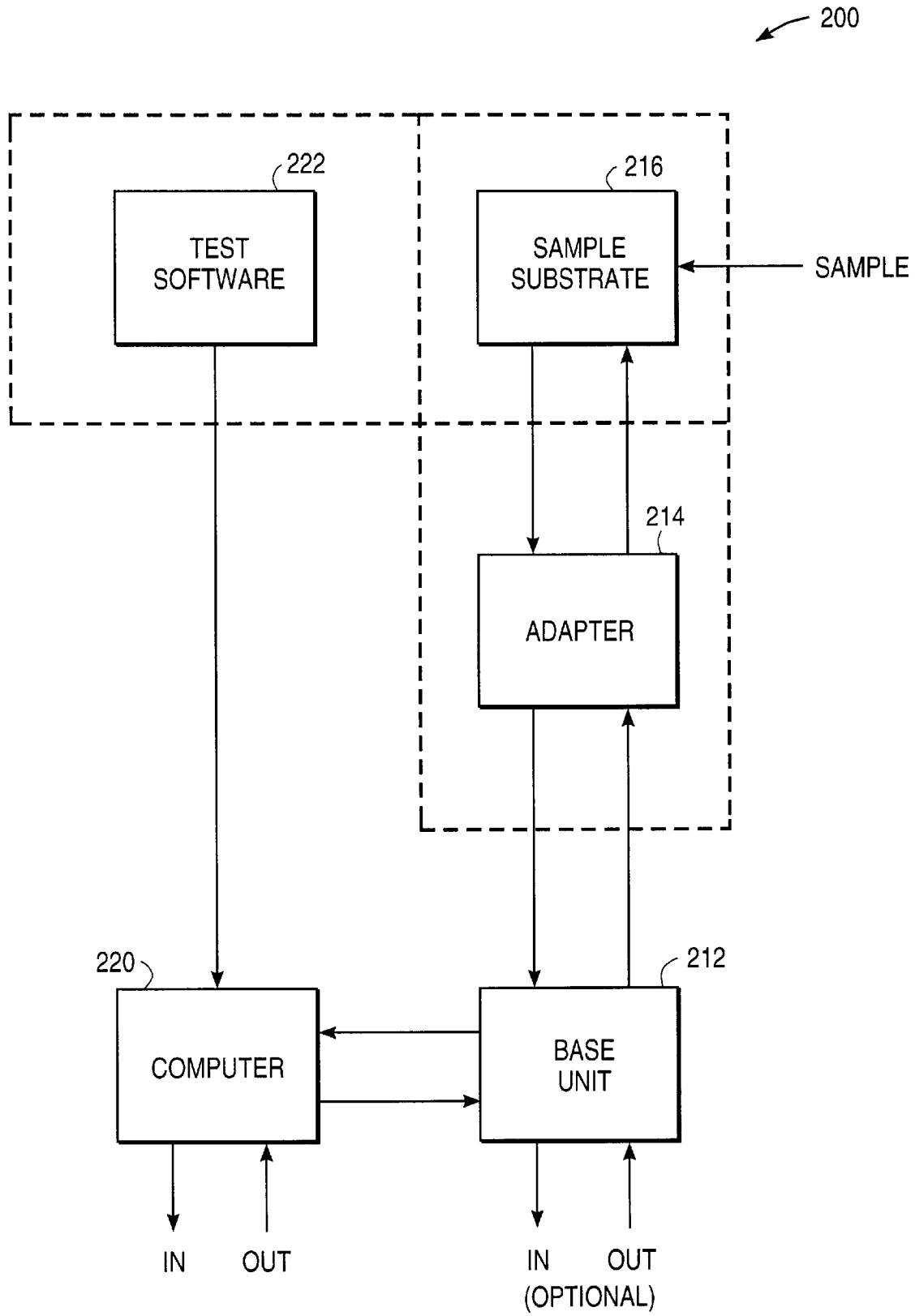
FIG. 3 is a block diagram illustrating the information flow between various components of the system of the present invention.

Referring now to FIG. 3, a system 200 according to the present invention can be configured in a wide variety of ways. For example, a base unit 212 may comprise a single monolithic instrument containing all control and analysis components necessary for performing an assay (in combination with adapter 214 and sample substrate 216), needing only to be connected to line current or other power source. The base unit 212, however, will be connected to a general purpose computer 220, e.g. a personal computer or work station, which provides at least a portion of the input/output, control, and computational functions of the system 200. The computer 220 may be connected by any conventional connectors, typically using serial or parallel input ports. The computer will be programmed using software 222, which may be in the form of any conventional computer medium. The software will comprise instructions for all or a portion of the computer functions. For example, the software may comprise the operating system utilized in performing all assays using the system of the present invention. Alternatively, the computer may utilized a conventional operating system capable of controlling real time functions, as set forth above. The system test software 222 will usually include system instructions which are general and apply to many assays as well as system instructions which are specific for any particular assay. The instructions may be included in a single disk or other medium, or may be included in multiple disks which may then be combined in a desired manner for performing a particular assay. Alternatively, the test software may be downloaded into the base unit and/or onto a storage medium via a network, the internet, or otherwise as set forth above. The system software will include functions such as system initialization, assay format, computational instructions, user/patient input instructions, and the like.

Thus, it can be seen, that the base unit 212 and computer 220 will generally be useful for performing many different types of assays, while the adapter 214 and sample substrate 216 will be more specifically directed at particular assay(s). One type of adapter 214 may be compatible with multiple sample substrates 216 intended for performing two or more different assays, where the system test software 222 can enable the adapter 214 and base unit 212 to properly interface with the sample substrate 216. Systems according to the present invention will thus further comprise the combination of test hardware 222 with either an adapter 214, sample substrate(s) 216, or both. That is, a user already possessing a monolithic base unit 212 or combination base unit 212 and computer 220, may later acquire the combination of system test software 222 and adapter 214 intended to perform a particular assay or assays. By then mounting the adapter 214 on the base unit and loading the software 222 onto the computer 220/base unit 212, the system will be configured to receive sample substrates to analyze particular test specimens for the desired analyte. Alternatively, when an adapter 214 is suitable for two or more assays, the user may later acquire the combination of test software 222 and sample substrate(s) 216 which enable the preexisting combination of computer 220, base unit 212, and adapter 214 to perform a new assay. In some cases, the combination of adapter 214, sample substrate(s) 216, and system test software 222 will also be provided to the user.

Figure 4:
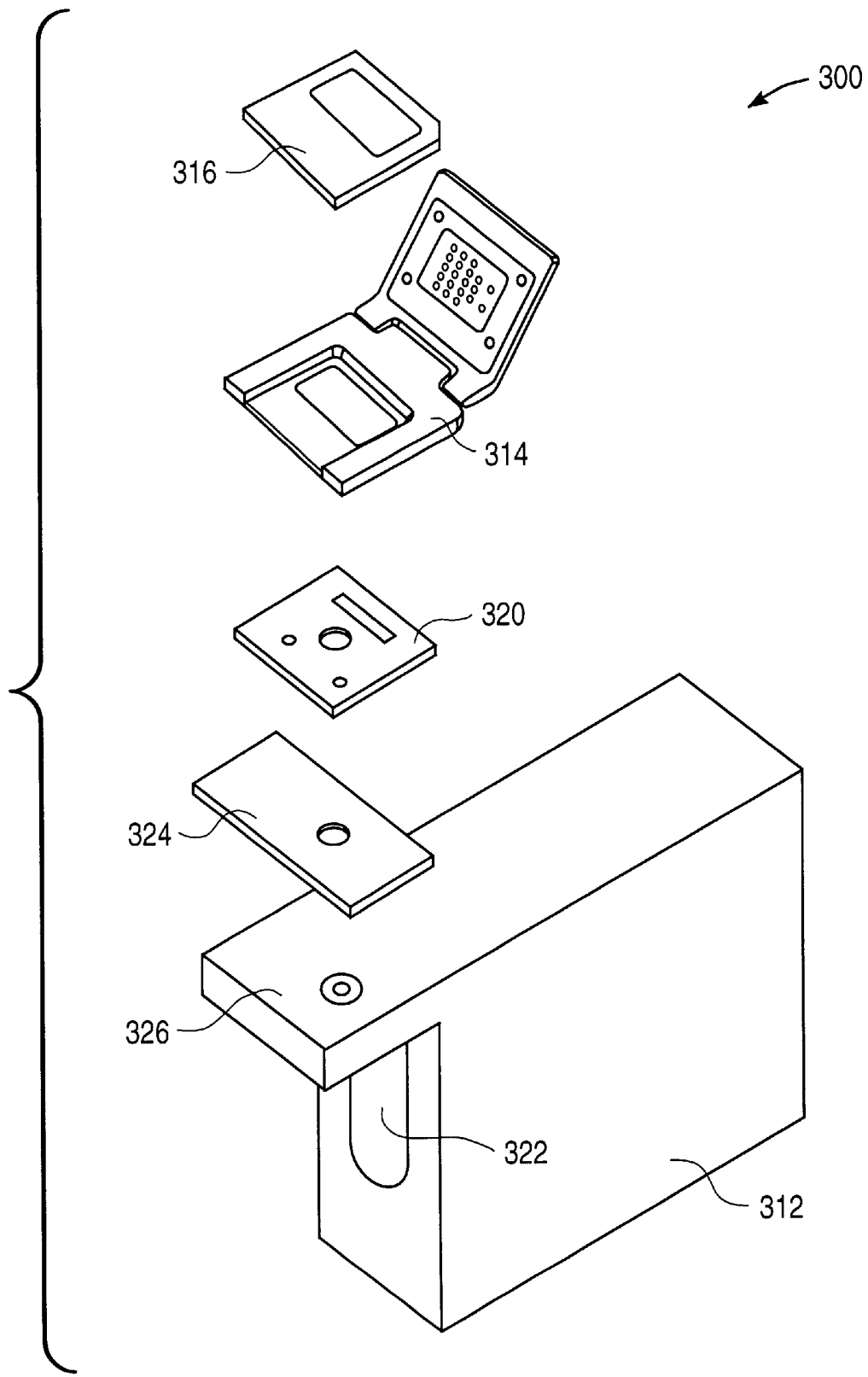
FIG. 4 illustrates an exemplary analytical system incorporating the components of the system of the present invention.

Referring now to FIG. 4, an exemplary system 300 configuration is illustrated. The system 300 comprises a base unit 312, an adapter 314, and a sample substrate 316. Additionally, a universal adapter 320 is provided as a discrete component for removable or permanent mounting onto the base unit 312. The universal adapter 320 defines the attachment region on the base unit 312 for receiving the adapter 314. Base unit 312 provides system functions, such as an optical source/detector 322 and a heater plate 324. The universal adapter 320 is mounted over the heater plate 324 onto a support surface 326 of the base unit 312. The base unit 312 is then ready to removably receive adapter plate(s) 314 which in turn is ready to receive sample substrates 316. The various interfaces among the system components may follow any of the patterns described above in connection with the systems of FIGS. 1 and 2. Use of the universal adapter 320 is advantageous since it facilitates standardization of the interface between the base unit 312 and the adapter 314. Also, a single base unit 312 (or base unit design) can be interfaced with an even wider range of adapters 314 by employing different classes or types of universal adapters, each of which can display alternative functionalities and interconnection patterns.

Although the foregoing invention has been described in some detail by way of illustration and example, for purposes of clarity of understanding, it will be obvious that certain changes and modifications may be practiced within the scope of the appended claims.

What is claimed is:

1. An analytical system comprising:
   a sample substrate having a plurality of mesoscale channels disposed therein, the plurality of channels connecting a plurality of reservoirs, each of the plurality of channels having at least one cross-sectional dimension between about 0.1 and 500 μm;
   a base unit comprising an electrical power supply;
   a sample substrate interface array attached to the base unit and comprising:
      a sample substrate attachment region including a plurality of electrical connectors disposed thereon, the electrical connectors being electrically coupled to the electrical power supply and being positioned within the substrate attachment region to provide electrical connection between the plurality of reservoirs and the electrical power supply when the substrate is placed, in the substrate attachment region wherein the electrical connectors comprise pin electrodes disposed on the interface array, the pin electrodes being positioned to directly engage fluids present in the reservoirs; and
   an energy emission detector disposed in the base unit and positioned to detect energy emitted from at least one of the channels disposed in the sample substrate, when the sample substrate is placed in the sample substrate attachment region.

2. The analytical system of claim 1, wherein the substrate attachment region comprises a hinged cover, the pin electrodes being positioned on the hinged cover to directly engage fluids present in the reservoirs when the cover is closed over the sample substrate.

3. The analytical system of claim 1, wherein the energy emission detector comprises an optical detector.

4. The analytical system of claim 3, wherein the optical detector comprises an optical source/detector.

5. The analytical system of claim 4, wherein the optical source/detector comprises a fluorescence detector.

6. The system of claim 1, further comprising a computer operably coupled to the base unit, the computer comprising appropriate software for instructing interfacing between the base unit and the sample substrate.

7. The analytical system of claim 1, wherein the sample substrate interface array is disposed on an adapter, the adapter being removably attached to the base unit, the adapter providing electrical connection between the plurality of electrical connectors on the sample substrate interface array and the electrical power supply in the base unit.

8. An analytical system comprising:
   a sample substrate having a plurality of mesoscale channels disposed therein, the plurality of channels connecting a plurality of reservoirs, each of the plurality of channels having at least one cross-sectional dimension between about 0.1 and 500 μm;
   a base unit comprising an electrical power supply;
   a sample substrate interface array attached to the base unit and comprising:
      a sample substrate attachment region including a plurality of electrical connectors disposed thereon, the electrical connectors being electrically coupled to the electrical power supply and being positioned within the substrate attachment region to provide electrical connection between the plurality of reservoirs and the electrical power supply when the substrate is placed in the substrate attachment region, wherein the electrical connectors on the sample attachment region comprise electrical contacts that are positioned to establish electrical contact with a plurality of corresponding electrical contacts on the microfluidic device when the microfluidic device is placed in the substrate attachment region, the electrical contacts on the microfluidic device providing an electrical connection to the plurality of reservoirs; and an energy emission detector disposed in the base unit and positioned to detect energy emitted from at least one of the channels disposed in the sample substrate, when the sample substrate is placed in the sample substrate attachment region.

9. The analytical system of claim 8, wherein the substrate attachment region comprises a hinged cover, the electrical contacts on the substrate attachment region being positioned on the hinged cover to contact the plurality of corresponding electrical contacts on the sample substrate when the hinged cover is closed.

10. The analytical system of claim 8, wherein the electrical connectors on the sample attachment region are selected from pins, plugs, zero insertion force (ZIF) connectors and edge connectors.

11. The analytical system of claim 8, wherein the energy emission detector comprises an optical detector.

12. The analytical system of claim 11, wherein the optical detector comprises an optical source/detector.

13. The analytical system of claim 12, wherein the optical source/detector comprises a fluorescence detector.

14. The system of claim 8, further comprising a computer operably coupled to the base unit, the computer comprising appropriate software for instructing interfacing between the base unit and the sample substrate.

15. The analytical system of claim 8, wherein the sample substrate interface array is disposed on an adapter, the adapter being removably attached to the base unit, the adapter providing electrical connection between the plurality of electrical connectors on the sample substrate interface array and the electrical power supply in the base unit.

* * * * *